United States Patent
Kikuchi et al.

(10) Patent No.: US 12,202,848 B2
(45) Date of Patent: Jan. 21, 2025

(54) PHOSPHORAMIDITE ACTIVATOR

(71) Applicant: FUJIFILM WAKO PURE CHEMICAL CORPORATION, Osaka (JP)

(72) Inventors: Seiho Kikuchi, Saitama (JP); Kimihiko Sano, Saitama (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 57 days.

(21) Appl. No.: 17/768,354

(22) PCT Filed: Oct. 13, 2020

(86) PCT No.: PCT/JP2020/038612
§ 371 (c)(1),
(2) Date: Apr. 12, 2022

(87) PCT Pub. No.: WO2021/075423
PCT Pub. Date: Apr. 22, 2021

(65) Prior Publication Data
US 2024/0166674 A1 May 23, 2024

(30) Foreign Application Priority Data
Oct. 18, 2019 (JP) ................. 2019-190698

(51) Int. Cl.
*C07F 9/6524* (2006.01)
*C07F 9/09* (2006.01)
*C07F 9/165* (2006.01)

(52) U.S. Cl.
CPC .............. *C07F 9/6524* (2013.01); *C07F 9/09* (2013.01); *C07F 9/165* (2013.01)

(58) Field of Classification Search
CPC ........... C07F 9/6524; C07F 9/09; C07F 9/165

USPC ........................................................ 544/251
See application file for complete search history.

(56) References Cited

U.S. PATENT DOCUMENTS

2005/0267300 A1 12/2005 Manoharan et al.
2006/0178509 A1 8/2006 Reddy

FOREIGN PATENT DOCUMENTS

| EP | 1 848 730 | 3/2010 |
| JP | 2007-531794 | 11/2007 |
| JP | 2008-530092 | 8/2008 |

OTHER PUBLICATIONS

International Search Report issued in International Application No. PCT/JP2020/038612, Dec. 8, 2020, 5 pages w/translation.
Brill, et al., "Synthesis of Deoxydinucleoside Phosphorodithioates", J. Am. Chem. Soc., vol. 113, No. 10, 1991, pp. 3972-3980.
Sanghi, et al., "Improved Process for the Preparation of Nucleosidic Phosphoramidites Using a Safer and Cheaper Activator", Organic Process Research & Development, vol. 4, No. 3, 2000, pp. 175-181.
Extended European Search Report issued in correspond European Patent Application No. 20877708.6, May 12, 2023, 4 pages.

*Primary Examiner* — Kristin A Vajda
(74) *Attorney, Agent, or Firm* — HSML P.C.

(57) ABSTRACT

The present invention has an object to provide a phosphoramidite activator that improves a solubility of 5-benzylthio-1H-tetrazole in acetonitrile and does not reduce the yield and a purity of a target product.

The present invention relates to a phosphoramidite activator containing (i) at least one compound that is selected from the group consisting of piperidine, pyrrolidine, N-alkylpiperidine, and N-alkylpyrrolidine, (ii) 5-benzylthio-1H-tetrazole, and (iii) acetonitrile; and a method for activating a phosphoramidite and a method for synthesizing a phosphate ester or a thiophosphate ester, both methods using the activator.

10 Claims, No Drawings

PHOSPHORAMIDITE ACTIVATOR

TECHNICAL FIELD

The present invention relates to a phosphoramidite activator, a method for activating a phosphoramidite using the activator, and a method for synthesizing a phosphate ester or a thiophosphate ester.

BACKGROUND ART

A nucleic acid which is a generic term for a deoxyribonucleic acid (DNA) and a ribonucleic acid (RNA) is one kind of biopolymer having a structure in which nucleotides as a constitutional unit are linked in chains through phosphate ester bonds (phosphodiester bonds). Chemical synthesis (artificial synthesis) of the nucleic acid is an important technique in biochemistry and there is a demand for development of a method for synthesizing a nucleic acid in a high yield and a high purity.

The nucleic acid synthesis is usually performed by extending a nucleic acid chain by repeating a series of reaction cycles involving (A) deprotection of nucleosides or oligonucleotides, (B) a coupling reaction, (C) capping of unreacted substances, and (D) an oxidation or sulfurization reaction for coupling products. In recent years, a "solid-phase synthesis method" which is quick, simple, and can thus be automated has often been adopted and used. In addition, nucleic acid synthesis by a "phosphoramidite method" using a phosphoramidite in (B) the coupling reaction is the mainstream. Specific examples of the reaction cycle in the phosphoramidite method are shown below.

(In the reaction cycle, Ac represents an acetyl group, Base represents a nucleobase selected from adenine, guanine, cytosine, thymine, and uracil, DMTr represents a 4,4'-dimethoxytrityl group, iPr represents an isopropyl group, A represents a tert-butyldimethylsilyl group, a nucleotide, or an oligonucleotide, and M represents an oxygen atom or a sulfur atom.)

In the phosphoramidite method, an activator of a phosphoramidite is indispensable in a case where (B) the coupling reaction is performed. To date, various phosphoramidite activators, for example, ranging from 1H-tetrazole to 5-methylthio-1H-tetrazole (MTT), 5-ethylthio-1H-tetrazole (ETT), 5-nitrophenyl-1H-tetrazole (NPT), 4,5-dicyanoimidazole (DCI), and the like have been developed, and particularly in recent years, 5-benzylthio-1H-tetrazole (BTT; also referred to as 5-benzylmercapto-1H-tetrazole (BMT)) among various phosphoramidite activators has been noted as being useful.

Acetonitrile is generally used as a solvent in the nucleic acid synthesis by the phosphoramidite method. On the other hand, the BTT has a poor solubility in acetonitrile and BTT crystals precipitate at a low temperature in a high-concentration BTT-acetonitrile solution, which may cause a concern of a piping in a nucleic acid synthesizer being clogged. For that reason, in a case where BTT in acetonitrile is at a relatively high concentration, the concentration of the BTT-acetonitrile solution, which enables the solution to be stored and used, is limited to 0.25 mol/L, regardless of whether the phosphoramidite can be activated more quickly and efficiently.

Therefore, in order to improve the solubility of BTT in acetonitrile, Patent Literature 1 discloses a phosphoramidite activator to which N-alkylimidazole has been added as a co-solvent.

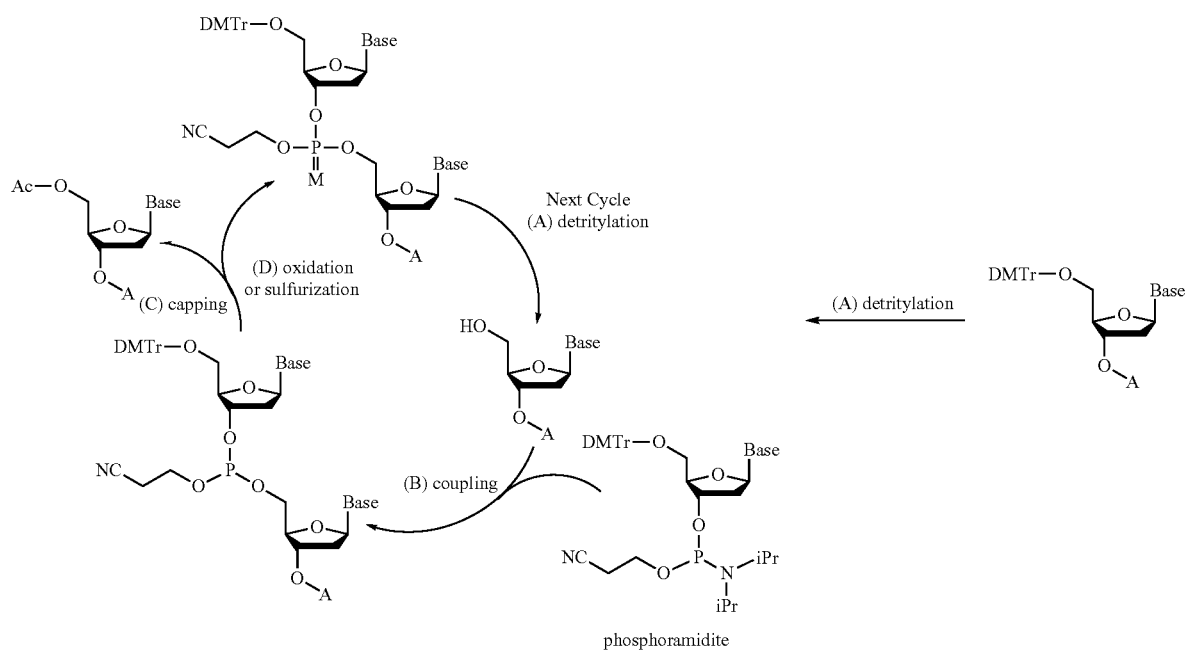

phosphoramidite

CITATION LIST

Patent Literature

Patent Literature 1: JP2008-530092A

SUMMARY OF INVENTION

Technical Problem

However, the phosphoramidite activator described in Patent Literature 1 had an improved solubility of BTT in acetonitrile by the addition of N-alkylimidazole, but had a problem in that the yield and the purity of a target product are lower than those in a case of using a phosphoramidite activator consisting of a BTT-acetonitrile solution without addition of N-alkylimidazole.

The present invention has been made in view of such circumstances, and has an object to provide an excellent phosphoramidite activator that solves the problem; and a method for activating a phosphoramidite and a method for synthesizing a phosphate ester or a thiophosphate ester, both methods using the activator.

Solution to Problem

The present inventors have conducted extensive investigations, and as a result, they have found that an excellent phosphoramidite activator having an improved solubility of BTT in acetonitrile and having no reduction in the yield and the purity of a target product can be obtained by the addition of at least one compound selected from the group consisting of piperidine, pyrrolidine, N-alkylpiperidine, and N-alkylpyrrolidine to a BTT-acetonitrile solution, thereby leading to completion of the present invention.

That is, the present invention encompasses the following inventions [i] to [xi].

[i] A phosphoramidite activator (which may hereinafter be simply referred to as the phosphoramidite activator of an embodiment of the present invention) containing (i) at least one compound selected from the group consisting of piperidine, pyrrolidine, N-alkylpiperidine, and N-alkylpyrrolidine, (ii) 5-benzylthio-1H-tetrazole, and (iii) acetonitrile.

[ii] The phosphoramidite activator as described in the invention [i], in which (i) is N-alkylpiperidine or N-alkylpyrrolidine.

[iii] The phosphoramidite activator as described in the invention [i] or [ii], in which (i) is N-methylpiperidine or N-methylpyrrolidine.

[iv] The phosphoramidite activator as described in any one of the inventions [i] to [iii], in which a molar concentration of (ii) is 0.25 mol/L or more.

[v] The phosphoramidite activator as described in any one of the inventions [i] to [iv], in which a molar concentration of piperidine of (i) is 17.0% or more with respect to a molar concentration of (ii), a molar concentration of pyrrolidine of (i) is 20.0% or more with respect to the molar concentration of (ii), a molar concentration of N-alkylpiperidine of (i) is 13.7% or more with respect to the molar concentration of (ii), and a molar concentration of N-alkylpyrrolidine of (i) is 16.0% or more with respect to the molar concentration of (ii).

[vi] The phosphoramidite activator as described in any one of the inventions [i] to [v], in which a molar concentration of piperidine of (i) is 17.0% or more with respect to a molar concentration of (ii), a molar concentration of pyrrolidine of (i) is 24.0% or more with respect to the molar concentration of (ii), and a molar concentration of N-alkylpiperidine or N-alkylpyrrolidine of (i) is 19.3% or more with respect to the molar concentration of (ii).

[vii] A method for activating a phosphoramidite (which may hereinafter be simply referred to as the activation method of an embodiment of the present invention), containing reacting a phosphoramidite with the phosphoramidite activator as described in any one of the inventions [i] to [vi].

[viii] The method for activating a phosphoramidite as described in the invention [vii], in which the phosphoramidite is a compound represented by the following general formula (I):

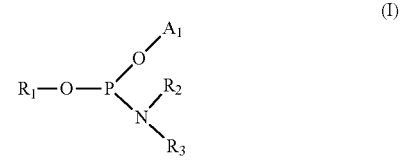

[in the general formula (I), $R_1$ represents a group selected from the following group (I-1) of functional groups:

Group (I-1) of functional groups

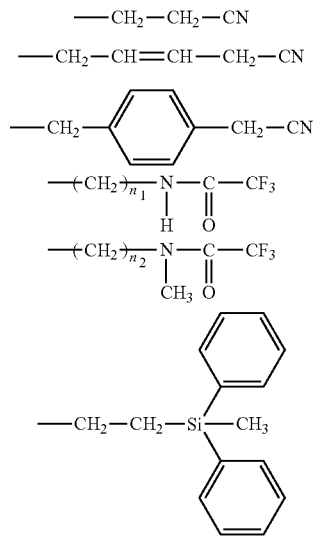

(in the group (I-1) of functional groups, $n_1$ and $n_2$ each independently represent an integer of 1 to 6), and $R_2$ and $R_3$ each independently represent an alkyl group having 1 to 6 carbon atoms, $R_2$ and $R_3$ may be bonded to form a 5- to 7-membered heterocyclic structure, and $A_1$ represents a nucleoside].

[ix] A method for synthesizing a phosphate ester or a thiophosphate ester (which may hereinafter be simply referred to as the synthesis method of an embodiment of the present invention), containing (1) reacting a phosphoramidite with a nucleoside or an oligonucleotide in the presence of the phosphoramidite activator as described in any one of the inventions [i] to [vi] to produce a phosphite ester; and (2) oxidizing or sulfurizing the phosphite ester to produce a phosphate ester or a thiophosphate ester.

[x] The method for synthesizing a phosphate ester or a thiophosphate ester as described in the invention [ix], in which the phosphoramidite is a compound represented by the following general formula (I), the phosphate ester is a compound represented by the following general formula (II-1), and the thiophosphate ester is a compound represented by the following general formula (II-2):

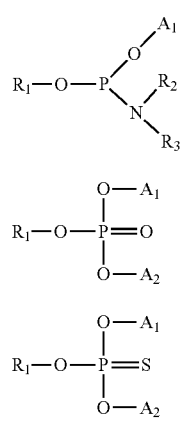

[in the general formulae (I), (II-1), and (II-2), $R_1$ represents a group selected from the following group (I-1) of functional groups:

Group (I-1) of functional groups

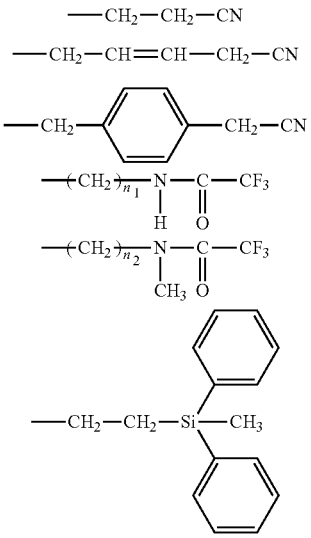

(in the group (I-1) of functional groups, $n_1$ and $n_2$ each independently represent an integer of 1 to 6), and $R_2$ and $R_3$ each independently represent an alkyl group having 1 to 6 carbon atoms, $R_2$ and $R_3$ may be bonded to form a 5- to 7-membered heterocyclic structure, $A_1$ represents a nucleoside, and $A_2$ represents a nucleoside or an oligonucleotide].

Advantageous Effects of Invention

It is possible to efficiently activate a phosphoramidite by using the phosphoramidite activator of the embodiment of the present invention, thereby obtaining a target product in a high yield and a high purity.

DESCRIPTION OF EMBODIMENTS

Phosphoramidite Activator of Embodiment of Present Invention

The phosphoramidite activator of the embodiment of the present invention contains (i) at least one compound selected from the group consisting of piperidine, pyrrolidine, N-alkylpiperidine, and N-alkylpyrrolidine, (ii) 5-benzylthio-1H-tetrazole, and (iii) acetonitrile.

Examples of the alkyl group in the N-alkylpiperidine and N-alkylpyrrolidine of (i) include an alkyl group having 1 to 6 carbon atoms, and among those, an alkyl group having 1 to 3 carbon atoms is preferable. In addition, the alkyl group may be linear, branched, or cyclic, and is preferably linear or branched. Specific examples thereof include a methyl group, an ethyl group, an n-propyl group, an isopropyl group, an n-butyl group, an isobutyl group, an n-pentyl group, an isopentyl group, an n-hexyl group, and an isohexyl group, the methyl group, the ethyl group, the n-propyl group, or the isopropyl group is preferable, and the methyl group is particularly preferable.

Specific examples of the N-alkylpiperidine of (i) include N-methylpiperidine, N-ethylpiperidine, N-n-propylpiperidine, N-isopropylpiperidine, N-n-butylpiperidine, N-isobutylpiperidine, N-n-pentylpiperidine, N-isopentylpiperidine, N-n-hexylpiperidine, and N-isohexylpiperidine, N-methylpiperidine, N-ethylpiperidine, N-n-propylpiperidine, or N-isopropylpiperidine is preferable, and N-methylpiperidine is particularly preferable.

Specific examples of the N-alkylpyrrolidine of (i) include N-methylpyrrolidine, N-ethylpyrrolidine, N-n-propylpyrrolidine, N-isopropylpyrrolidine, N-n-butylpyrrolidine, N-isobutylpyrrolidine, and N-n-pentylpyrrolidine, N-isopentylpyrrolidine, N-n-hexylpyrrolidine, and N-isohexylpyrrolidine, N-methylpyrrolidine, N-ethylpyrrolidine, N-n-propylpyrrolidine, or N-isopropylpyrrolidine is preferable, and N-methylpyrrolidine is particularly preferable.

(i) may contain only any one of or a combination of two or more of piperidine, pyrrolidine, N-alkylpiperidine, or N-alkylpyrrolidine.

As (i), any one compound selected from the group consisting of piperidine, pyrrolidine, N-alkylpiperidine, and N-alkylpyrrolidine is preferable, any one compound selected from the group consisting of piperidine, N-alkylpiperidine and N-alkylpyrrolidine is more preferable, N-alkylpiperidine or N-alkylpyrrolidine is still more preferable, and N-methylpiperidine or N-methylpyrrolidine is even still more preferable.

A lower limit value of the molar concentration of (ii) is usually 0.20 mol/L or more, preferably 0.25 mol/L or more, and still more preferably 0.30 mol/L or more with respect to a total volume of the phosphoramidite activator of the embodiment of the present invention. An upper limit value of the molar concentration of (ii) is usually 1.00 mol/L or less, preferably 0.50 mol/L or less, and more preferably 0.40 mol/L or less with respect to the total volume of the phosphoramidite activator of the embodiment of the present invention.

A lower limit value of the molar concentration of piperidine of (i) is preferably 17.0% or more with respect to a molar concentration of (ii); and an upper limit value of the molar concentration of piperidine of (i) is usually 150% or less, preferably 100% or less, and more preferably 50.0% or less with respect to the molar concentration of (ii).

A lower limit value of the molar concentration of pyrrolidine of (i) is preferably 20.0% or more, and more preferably 24.0% or more with respect to the molar concentration of (ii); and an upper limit value of the molar concentration of pyrrolidine of (i) is usually 150% or less, preferably 100% or less, and more preferably 50.0% or less with respect to the molar concentration of (ii).

A lower limit value of the molar concentration of N-alkylpiperidine of (i) is preferably 13.7% or more, and more preferably 19.3% or more with respect to the molar concentration of (ii); and an upper limit value of the molar concentration of N-alkylpiperidine of (i) is usually 150% or less, preferably 100% or less, and more preferably 50.0% or less with respect to the molar concentration of (ii).

A lower limit value of the molar concentration of N-alkylpyrrolidine of (i) is preferably 16.0% or more, and more preferably 19.3% or more with respect to the molar concentration of (ii); and an upper limit value of the molar concentration of N-alkylpyrrolidine of (i) is usually 150% or less, preferably 100% or less, and more preferably 50.0% or less with respect to the molar concentration of (ii).

The phosphoramidite activator of the embodiment of the present invention may contain components other than (i) at least one compound selected from the group consisting of piperidine, pyrrolidine, N-alkylpiperidine, and N-alkylpyrrolidine, (ii) 5-benzylthio-1H-tetrazole, and (iii) acetonitrile, but preferably consists of only (i), (ii), and (iii); more preferably consists of, among those, only (i) any one compound selected from the group consisting of piperidine, pyrrolidine, N-alkylpiperidine, and N-alkylpyrrolidine, (ii) 5-benzylthio-1H-tetrazole at 0.25 mol/L or more, and (iii) acetonitrile; and more preferably consists of, among those, only (i) any one compound selected from the group consisting of piperidine, pyrrolidine, N-alkylpiperidine, and N-alkylpyrrolidine, (ii) 5-benzylthio-1H-tetrazole at 0.25 mol/L or more, and (iii) acetonitrile (iii), in which the molar concentration of piperidine of (i) is 17.0% or more with respect to the molar concentration of (ii), the molar concentration of pyrrolidine of (i) is 20.0% or more with respect to the molar concentration of (ii), the molar concentration of N-alkylpiperidine of (i) is 13.7% or more with respect to the molar concentration of (ii), and the molar concentration of N-alkylpyrrolidine of (i) is 16.0% or more with respect to the molar concentration of (ii). The phosphoramidite activator of the embodiment of the present invention even still more preferably consists of, among those, only (i) any one compound selected from the group consisting of piperidine, pyrrolidine, N-alkylpiperidine, and N-alkylpyrrolidine, (ii) 5-benzylthio-1H-tetrazole at 0.30 mol/L or more, and (iii) acetonitrile, in which the molar concentration of piperidine of (i) is 17.0% or more with respect to the molar concentration of (ii), the molar concentration of pyrrolidine of (i) is 24.0% or more with respect to the molar concentration of (ii), and the molar concentration of (i) N-alkylpiperidine or N-alkylpyrrolidine is 19.3% or more with respect to the molar concentration of (ii); and particularly preferably consists of only (i) N-alkylpiperidine or N-alkylpyrrolidine, (ii) 5-benzylthio-1H-tetrazole at 0.30 mol/L or more, and (iii) acetonitrile, in which the molar concentration of N-alkylpiperidine or N-alkylpyrrolidine of (i) is 19.3% or more with respect to the molar concentration of (ii).

As any of (i) piperidine, pyrrolidine, N-alkylpiperidine, and N-alkylpyrrolidine, (ii) 5-benzylthio-1H-tetrazole, and (iii) acetonitrile in the phosphoramidite activator of the embodiment of the present invention, a product that is commercially available or appropriately synthesized by a method known per se may be used.

The phosphoramidite activator of the embodiment of the present invention may be prepared by mixing (i), (ii), and (iii) in accordance with a method known per se. Specifically, for example, the phosphoramidite activator of the embodiment of the present invention can be prepared by appropriately setting the amounts of (i) and (ii) to be used to give desired molar concentrations, first mixing (i) and (iii), and then mixing (ii) therewith.

The preparation of the phosphoramidite activator of the embodiment of the present invention is not particularly limited as long as it is performed under preparation conditions (a temperature, a pressure, an atmosphere, and the like) which enable the mixing without affecting (i), (ii), and (iii), and for example, the phosphoramidite activator of the embodiment of the present invention may be prepared at 15° C. to 40° C. under a normal pressure (1 atm) and an inert gas atmosphere (for example, nitrogen and argon).

Activation Method of Present Invention

The activation method of the embodiment of the present invention contains a step of reacting a phosphoramidite with the phosphoramidite activator of the embodiment of the present invention.

The phosphoramidite in the activation method of the embodiment of the present invention is a monoamide derivative of a phosphite diester, and in the present invention, the phosphoramidite particularly refers to a nucleoside phosphoramidite in which a nucleoside is bonded to one ester moiety of the phosphite diester. The phosphoramidite in the activation method of the embodiment of the present invention is not particularly limited as long as it is usually used in this field, and a product that is commercially available or appropriately synthesized by a method known per se may be used.

The nucleoside in the phosphoramidite in the activation method of the embodiment of the present invention is a compound consisting of a nucleobase and a sugar, in which a hydroxy group at the 5' position (5'-OH group) is preferably protected by a protective group. Specific examples of the nucleobase include adenine, guanine, cytosine, thymine, and uracil, and derivatives thereof in which a part of the nucleobase is substituted or modified. Specific examples of the sugar include ribose and deoxyribose, and derivatives thereof in which a part of the sugar is modified. Examples of the protective group include an acetyl group, a tert-butyldiphenylsilyl group, a tert-butyldimethylsilyl group, a 4,4'-dimethoxytrityl group (4,4'-dimethoxytriphenylmethyl group), and a 4-monomethoxytrityl group (4-methoxytriphenylmethyl group), and the 4,4'-dimethoxytrityl group is preferable.

In addition, in a case where the nucleoside in the phosphoramidite in the activation method of the embodiment of the present invention has a hydroxy group at the 2' position (2'-OH group), it is preferable that the 2'-OH group is also protected by a protective group as in the 5'-OH group. Examples of the protective group include an acetyl group, a tert-butyldiphenylsilyl group, a tert-butyldimethylsilyl group, a triisopropylsiloxymethyl group, a 4,4'-dimethoxytrityl group, and a 4-monomethoxytrityl group, and the tert-butyldimethylsilyl group is preferable.

Furthermore, in the nucleoside in the phosphoramidite in the activation method of the embodiment of the present invention, a functional group other than the 5'-OH group or the 2'-OH group is preferably protected as necessary to prevent occurrence of a side reaction. Specifically, for example, in a case where the nucleoside in the phosphoramidite in the activation method of the embodiment of the present invention has adenine, guanine, or cytosine as the nucleobase, it is preferable that an amino group in the nucleobase is protected by an acyl group such as an acetyl group, an isobutyryl group, a benzoyl group, a 4-(tert-butyl) benzoyl group, and a phenoxyacetyl group.

Specific examples of the phosphoramidite in the activation method of the embodiment of the present invention include a compound represented by the following general formula (I).

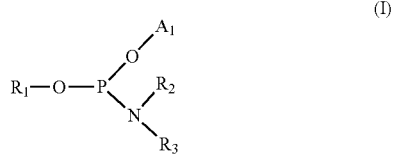

(I)

[In the general formula (I), $R_1$ represents a group selected from the following group (I-1) of functional groups:

Group (I-1) of functional groups

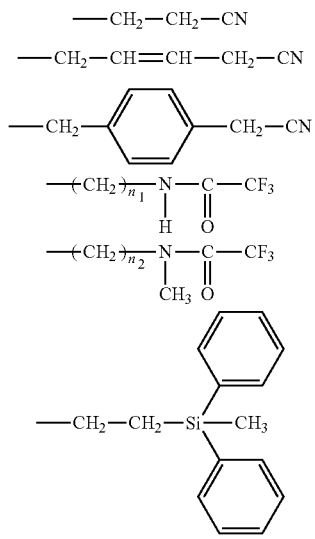

(in the group (I-1) of functional groups, $n_1$ and $n_2$ each independently represent an integer of 1 to 6), and
$R_2$ and $R_3$ each independently represent an alkyl group having 1 to 6 carbon atoms, $R_2$ and $R_3$ may be bonded to form a 5- to 7-membered heterocyclic structure, and
$A_1$ represents a nucleoside.]

$n_1$ and $n_2$ in the group (I-1) of functional groups of the general formula (I) are each preferably an integer of 2 to 5, and more preferably 2.

As the group (I-1) of functional groups of the general formula (I), a cyanoethyl group is particularly preferable.

As the alkyl group having 1 to 6 carbon atoms in $R_2$ and $R_3$ of the general formula (I), those having 2 or 3 carbon atoms are preferable. In addition, the alkyl group may be linear, branched, or cyclic, and is preferably branched. Specific examples thereof include a methyl group, an ethyl group, an n-propyl group, an isopropyl group, an n-butyl group, an isobutyl group, an n-pentyl group, an isopentyl group, a cyclopentyl group, an n-hexyl group, an isohexyl group, and a cyclohexyl group, the ethyl group, the n-propyl group, or the isopropyl group is preferable, and the isopropyl group is particularly preferable.

In a case where $R_2$ and $R_3$ in the general formula (I) are bonded to each other to form a 5- to 7-membered heterocyclic structure, the 5- to 7-membered heterocyclic structure may further have one or more heteroatoms, in addition to the nitrogen atom in the general formula (I) bonded to $R_2$ and $R_3$. Specific examples of the 5- to 7-membered ring heterocyclic structure include pyrrolidine, piperidine, hexamethyleneimine, oxazolidine, morpholine, thiazolidine, and thiomorpholine, and piperidine, morpholine, or thiomorpholine is preferable.

As $R_2$ and $R_3$ of the general formula (I), an alkyl group having 2 or 3 carbon atoms is preferable, and an isopropyl group is particularly preferable. In addition, it is preferable that $R_2$ and $R_3$ of the general formula (I) are the same.

The nucleoside in $A_1$ of the general formula (I) represents the same one as the nucleoside in the phosphoramidite in the activation method of the embodiment of the present invention.

As for the amount of the phosphoramidite activator of the embodiment of the present invention to be used, the content of (ii) 5-benzylthio-1H-tetrazole in the phosphoramidite activator of the embodiment of the present invention is usually an amount corresponding to 1 to 20 equivalents with respect to 1 mol of phosphoramidite.

The activation method of the embodiment of the present invention is not particularly limited as long as it is performed under reaction conditions (a temperature, a pressure, an atmosphere, and the like) which enable the phosphoramidite and the phosphoramidite activator of the embodiment of the present invention to react without delay, and the activation method may be performed, for example, at 10° C. to 40° C. and under a normal pressure and an inert gas atmosphere. The reaction time in the activation method of the embodiment of the present invention cannot be unequivocally determined since it can vary depending on the reaction conditions, but the reaction time is usually 1 minute to 3 hours.

Synthesis Method of Present Invention

The synthesis method of the embodiment of the present invention contains (1) a step of reacting a phosphoramidite with a nucleoside or an oligonucleotide in the presence of the phosphoramidite activator of the embodiment of the present invention to produce a phosphite ester, and (2) a step of oxidizing or sulfurizing the phosphite ester to produce a phosphate ester or a thiophosphate ester.

Examples of the phosphoramidite in the step (1) in the synthesis method of the embodiment of the present invention include the same ones as those of the phosphoramidite in the activation method of the embodiment of the present invention, and preferred ones thereof are also the same.

The nucleoside in the step (1) in the synthesis method of the embodiment of the present invention is not particularly limited as long as it is a natural or artificial nucleoside usually used in this field, and a product that is commercially available or appropriately synthesized by a method known per se may be used.

The nucleoside in the step (1) in the synthesis method of the embodiment of the present invention is a compound consisting of a nucleobase and a sugar, in which a hydroxy group at the 3' position (3'-OH group) is protected by a protective group. Specific examples of the nucleobase include adenine, guanine, cytosine, thymine, and uracil, and derivatives thereof in which a part of the nucleobase is substituted or modified. Specific examples of the sugar include ribose and deoxyribose, and derivatives thereof in which a part of the sugar is modified. Examples of the protective group include an acetyl group, a tert-butyldiphenylsilyl group, a tert-butyldimethylsilyl group, a 4,4'-dimethoxytrityl group, and a 4-monomethoxytrityl group, and the tert-butyldimethylsilyl group is preferable.

In addition, in a case where the nucleoside in the step (1) in the synthesis method of the embodiment of the present invention has a 2'-OH group, it is preferable that the 2'-OH group is also protected by a protective group as in the 3'-OH group. Examples of the protective group include an acetyl group, a tert-butyldiphenylsilyl group, a tert-butyldimethylsilyl group, a triisopropylsiloxymethyl group, a 4,4'-dimethoxytrityl group, and a 4-monomethoxytrityl group, and the tert-butyldimethylsilyl group is preferable.

In the nucleoside in the step (1) in the synthesis method of the embodiment of the present invention, a functional group other than the 3'-OH group or the 2'-OH group is preferably protected as necessary to prevent occurrence of a side reaction. Specifically, for example, in a case where the nucleoside in the step (1) in the synthesis method of the embodiment of the present invention has adenine, guanine, or cytosine as the nucleobase, it is preferable that an amino group in the nucleobase is protected by an acyl group such as an acetyl group, an isobutyryl group, a benzoyl group, a 4-(tert-butyl)benzoyl group, and a phenoxyacetyl group.

The oligonucleotide in the step (1) in the synthesis method of the embodiment of the present invention is not particularly limited as long as it is an oligonucleotide usually used in this field, and a product that is commercially available or appropriately synthesized by a method known per se may be used. Furthermore, the oligonucleotide also contains a phosphorothioate-type oligonucleotide. In addition, an oligonucleotide in which the 5' terminal of a "phosphate ester or thiophosphate ester" obtained by the synthesis method of the embodiment of the present invention is deprotected may be used as the oligonucleotide.

The oligonucleotide in the step (1) in the synthesis method of the embodiment of the present invention is preferably an oligonucleotide in which about 1 to 50 nucleosides are bonded through a phosphodiester bond or a phosphorothioate bond at the 3' and 5' positions, and a hydroxy group at the 3' terminal is protected by a protective group. Examples of the nucleoside include the same ones as those of the nucleoside in the step (1) in the synthesis method of the embodiment of the present invention, except that the 3'-OH group is not protected, and preferred ones thereof are also the same. A plurality of nucleosides in the oligonucleotide may be the same as or different from each other. Examples of the protective group at the 3' terminal of the oligonucleotide include the same ones as those of the protective group as the 3'-OH group of the nucleoside in the step (1) in the synthesis method of the embodiment of the present invention, and preferred ones thereof are also the same.

The nucleoside and the oligonucleotide in the step (1) in the synthesis method of the embodiment of the present invention may be those bonded on a carrier for solid-phase synthesis. The carrier for solid-phase synthesis is not particularly limited as long as it is usually used in this field, and specific examples thereof include porous glass, porous synthetic polymers (for example, polystyrene and polyacrylamide), and silica particles having a surface thereof coated with the resin.

An amount of the phosphoramidite used in the step (1) in the synthesis method of the embodiment of the present invention is usually 1 to 5 equivalents with respect to 1 mol of the nucleoside or the oligonucleotide.

With regard to the amount of the phosphoramidite activator of the embodiment of the present invention used in the step (1) in the synthesis method of the embodiment of the present invention, a content of (ii) 5-benzylthio-1H-tetrazole is usually an amount corresponding to 1 to 20 equivalents with respect to 1 mol of phosphoramidite.

The step (1) in the synthesis method of the embodiment of the present invention is not particularly limited as long as it is performed under reaction conditions (a temperature, a pressure, an atmosphere, and the like) which enable a reaction for producing a phosphite ester to proceed without delay, and the step (1) may be performed, for example, at 10° C. to 40° C. and under a normal pressure and an inert gas atmosphere. The reaction time of the step (1) in the synthesis method of the embodiment of the present invention cannot be unequivocally determined since it can vary depending on the reaction conditions, but is usually 1 minute to 3 hours.

The step (2) in the synthesis method of the embodiment of the present invention is a step of oxidizing the phosphite ester, which is a product of the step (1), with an oxidizing reagent to form a phosphate ester or of sulfurizing the phosphite ester with a sulfurizing reagent to form a thiophosphate ester.

The oxidizing reagent is not particularly limited as long as it is usually used in this field, and is preferably hydrous iodine. Specific examples thereof include a form of an iodine solution containing water as one of the solvents, and specific examples thereof include a pyridine-tetrahydrofuran-water mixed solvent and a pyridine-water mixed solvent. A concentration of iodine contained in the iodine solution is usually 0.02 to 0.10 mol/L with respect to the total volume of the solution.

The sulfurizing reagent is not particularly limited as long as it is usually used in this field, and specific examples thereof include phenylacetyl disulfide (PADS), 3H-1,2-benzodithiol-3-one-1,1-dioxide (Beaucage reagent), 5-phenyl-3H-1,2,4-dithiazol-3-one (POS), [(N,N-dimethylaminomethylidene)amino]-3H-1,2,4-dithiazoline-3-thione (DDTT). In addition, these may be used in a form of a solution, and specific examples thereof include a POS-containing acetonitrile solution having a concentration of 0.02 to 0.10 mol/L.

An amount of the oxidizing reagent or the sulfurizing reagent to be used is usually 1 to 5 equivalents with respect to 1 mol of the phosphite ester.

In a case where the phosphoramidite in the step (1) in the synthesis method of the embodiment of the present invention is a compound represented by the general formula (I), specific examples of the phosphite ester which is a product of the step (1) include a compound represented by the general formula (II-0). Specific examples of the phosphate ester which is a product in the step (2) include a compound represented by the following general formula (II-1), and specific examples of the thiophosphate ester which is a product of the step (2) include a compound represented by the following general formula (II-2).

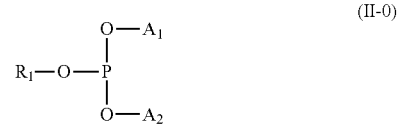

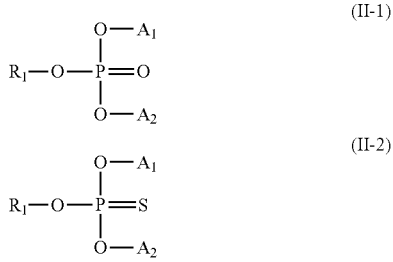

[In the general formulae (II-0) to (II-2), $R_1$ represents a group selected from the following group (I-1) of functional groups:

Group (I-1) of functional groups

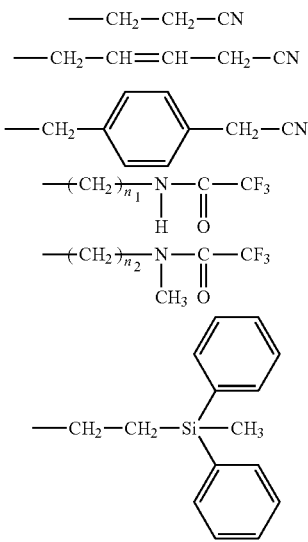

(in the group (I-1) of functional groups, $n_1$ and $n_2$ each independently represent an integer of 1 to 6), and $A_1$ represents a nucleoside and $A_2$ represents a nucleoside or an oligonucleotide.]

Examples of the group (I-1) of functional groups of the general formulae (II-0) to (II-2) include the same ones as those of the group (I-1) of functional groups of the general formula (I), and preferred ones are also the same.

Examples of the nucleoside in $A_1$ of the general formulae (II-0) to (II-2) include the same ones as those in the phosphoramidite in the activation method of the embodiment of the present invention, and preferred ones are also the same.

Examples of the nucleoside in $A_2$ of the general formulae (II-0) to (II-2) include the same ones as those in the step (1) in the synthesis method of the embodiment of the present invention, and preferred ones are also the same.

Examples of the oligonucleotide in $A_2$ of the general formulae (II-0) to (II-2) include the same ones as those of the oligonucleotide in the step (1) in the synthesis method of the embodiment of the present invention, and preferred ones are also the same.

The step (2) in the synthesis method of the embodiment of the present invention is not particularly limited as long as it is performed under reaction conditions (a temperature, a pressure, an atmosphere, and the like) which enable an oxidation reaction or a sulfurization reaction for a phosphite ester to proceed without delay, and the step (2) may be performed, for example, at 10° C. to 40° C. and under a normal pressure and an inert gas atmosphere. The reaction time of the step (2) in the synthesis method of the embodiment of the present invention cannot be unequivocally determined since it can vary depending on the reaction conditions, but is usually 1 minute to 3 hours.

As mentioned above, in the nucleic acid synthesis, a nucleic acid chain is usually extended by repeatedly performing four steps (reaction cycle) referred to as (A) deprotection of nucleosides or oligonucleotides, (B) a coupling reaction, (C) capping of unreacted substances, and (D) an oxidation or sulfurization reaction for coupling products. The step (1) in the synthesis method of the embodiment of the present invention corresponds to the step (B) in the nucleic acid synthesis, and the step (2) in the synthesis method of the embodiment of the present invention corresponds to the step (D) in the nucleic acid synthesis. Therefore, it is possible to extend the nucleic acid chain by repeating the reaction cycle containing the synthesis method of the embodiment of the present invention, thereby obtaining a desired nucleic acid.

The step (A) in the nucleic acid synthesis is a step of deprotecting the protective group at the 5' position of the nucleoside or the oligonucleotide with a deblocking reagent. The deblocking reagent is not particularly limited as long as it is usually used in this field, and a product that is commercially available or appropriately synthesized by a method known per se may be used. Specific examples thereof include a dichloroacetic acid-toluene solution and a trichloroacetic acid-dichloromethane solution.

The step (C) in the nucleic acid synthesis is a step of capping an unreacted substance in the step (B) in the nucleic acid synthesis, using a capping reagent. The capping reagent is not particularly limited as long as it is usually used in this field, and a product that is commercially available or appropriately synthesized by a method known per se may be used. Specific examples thereof include a combination of acetic anhydride and N-methylimidazole. These are usually used in the form of a solution, and specific examples of the solution include an acetonitrile solution, a pyridine-acetonitrile solution, a 2,6-lutidine-acetonitrile solution, a tetrahydrofuran solution, a pyridine-tetrahydrofuran solution, and a 2,6-lutidine-tetrahydrofuran solution.

In addition, in a case of the solid-phase synthesis method, the steps (A) to (D) in the nucleic acid synthesis are repeated to extend the nucleic acid chain, and then a target nucleic acid is cut out from a carrier for solid-phase synthesis and deprotected. Aqueous ammonia or a methylamine solution is usually used in this step. The aqueous ammonia is not particularly limited as long as it is usually used in this field, and a product that is commercially available or appropriately synthesized by a method known per se may be used. Specific examples thereof include an aqueous ammonia solution having a concentration of 25% to 28% by mass, which may be used in the form of a mixed solution of an aqueous methylamine solution and an aqueous ethanol solution.

Hereinafter, the present invention will be described in more detail with reference to Examples and Comparative Examples, but the present invention is not limited to these Examples.

EXAMPLES

Example 1 Method for Preparing Phosphoramidite Activator 1

Piperidine in an amount of 0.15 mL (1.52 mmol) was added to 29.85 mL of acetonitrile and dissolved to prepare a 0.5% by volume (volume percentage concentration; volume/volume %) piperidine-added acetonitrile solution. Next, 1.73 g (9.00 mmol) of 5-benzylthio-1H-tetrazole (BTT) (manufactured by FUJIFILM Wako Pure Chemical Corporation) was filled up to 30 mL with a 0.5% by volume piperidine-added acetonitrile solution to prepare a phosphoramidite activator 1 with 0.30 mol/L of BTT, containing 0.5% by volume of piperidine.

Examples 2 to 4 Method for Preparing Phosphoramidite Activators 2 to 4

Phosphoramidite activators 2 to 4 were prepared in the same manner as in Example 1, except that acetonitrile solutions to which 0.5% by volume of various additives described in Table 1 had been added were used instead of the 0.5% by volume piperidine-added acetonitrile solution.

Comparative Example 1 Method for Preparing Phosphoramidite Activator 101

A phosphoramidite activator 101 was prepared in the same manner as in Example 1, except that an acetonitrile solution containing no additive was used instead of the 0.5% by volume piperidine-added acetonitrile solution.

Comparative Examples 2 to 12 Method for Preparing Phosphoramidite Activators 102 to 112

Phosphoramidite activators 102 to 112 were prepared in the same manner as in Example 1, except that acetonitrile solutions to which 0.5% by volume of various additives described in Table 1 had been added were used instead of the 0.5% by volume piperidine-added acetonitrile solution.

Experimental Example 1 Evaluation 1 of Storage Stability of Phosphoramidite Activator The presence or absence of precipitation (the presence of absence of precipitation of BTT crystals) after leaving each of the phosphoramidite activators 1 to 4 obtained in Examples 1 to 4 and the phosphoramidite activators 101 to 112 obtained in Comparative Examples 1 to 12 to stand at 0° C. to 2° C. for one week and two weeks, respectively, was confirmed.

The evaluation results are shown in Table 1. In addition, a ratio of the molar concentration (mol/L) of the additive to the molar concentration (mol/L) of BTT is shown in Table 1 together with the evaluation results as "a ratio (%) to BTT".

TABLE 1

| | Molar concentration (mol/L) of BTT | Additive | | | | Presence or absence of precipitation | |
|---|---|---|---|---|---|---|---|
| | | Type | Addition amount | Molar concentration (mol/L) | Ratio (%) to BTT | After one week | After two weeks |
| Example 1: Phosphoramidite activator 1 | 0.30 | Piperidine | 0.5 | 0.051 | 17.0 | Absence | Absence |
| Example 2: Phosphoramidite activator 2 | 0.30 | Pyrrolidine | 0.5 | 0.060 | 20.0 | Absence | Presence |
| Example 3: Phosphoramidite activator 3 | 0.30 | N-methylpiperidine | 0.5 | 0.041 | 13.7 | Absence | Presence |
| Example 4: Phosphoramidite activator 4 | 0.30 | N-methylpyrrolidine | 0.5 | 0.048 | 16.0 | Absence | Presence |
| Comparative Example 1 Phosphoramidite activator 101 | 0.30 | (None) | — | — | — | Presence | Presence |
| Comparative Example 2: Phosphoramidite activator 102 | 0.30 | Tetrahydrofuran | 0.5 | 0.061 | 20.3 | Presence | Presence |
| Comparative Example 3: Phosphoramidite activator 103 | 0.30 | Toluene | 0.5 | 0.047 | 15.7 | Presence | Presence |
| Comparative Example 4: Phosphoramidite activator 104 | 0.30 | N,N-dimethylformamide | 0.5 | 0.065 | 21.7 | Presence | Presence |
| Comparative Example 5: Phosphoramidite activator 105 | 0.30 | N-methylpyrrolidone | 0.5 | 0.052 | 17.3 | Presence | Presence |
| Comparative Example 6: Phosphoramidite activator 106 | 0.30 | Dimethylsulfoxide | 0.5 | 0.070 | 23.3 | Presence | Presence |
| Comparative Example 7: Phosphoramidite activator 107 | 0.30 | Pyridine | 0.5 | 0.062 | 20.7 | Presence | Presence |
| Comparative Example 8: Phosphoramidite activator 108 | 0.30 | Triethylamine | 0.5 | 0.036 | 12.0 | Presence | Presence |
| Comparative Example 9: Phosphoramidite activator 109 | 0.30 | Diisopropylamine | 0.5 | 0.035 | 11.7 | Presence | Presence |
| Comparative Example 10: Phosphoramidite activator 110 | 0.30 | 1-Methyl-1H-tetrazole | 0.5 | 0.047 | 15.7 | Presence | Presence |
| Comparative Example 11: Phosphoramidite activator 111 | 0.30 | 1-Methylpyrazole | 0.5 | 0.060 | 20.0 | Presence | Presence |
| Comparative Example 12: Phosphoramidite activator 112 | 0.30 | Pyrazine | 0.5 | 0.049 | 16.3 | Presence | Presence |

Furthermore, the structure of an additive used for each phosphoramidite activator is as follows.

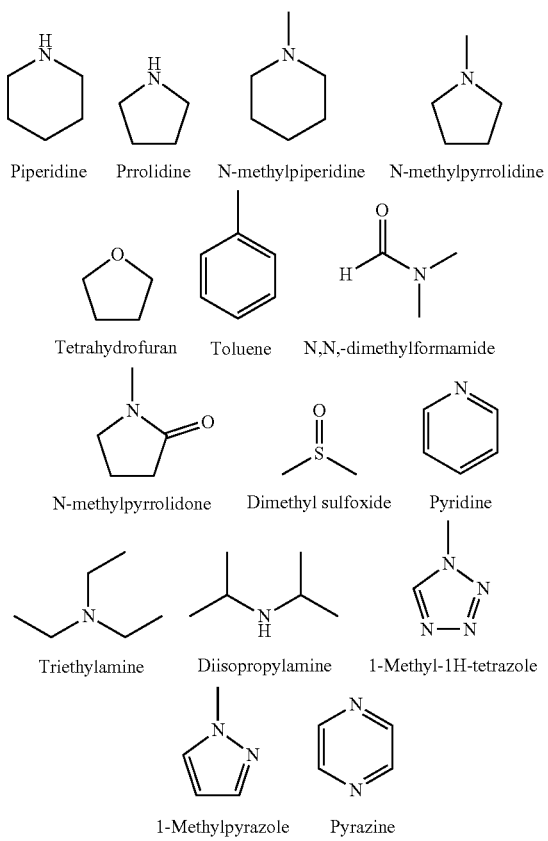

Piperidine  Prrolidine  N-methylpiperidine  N-methylpyrrolidine

Tetrahydrofuran  Toluene  N,N,-dimethylformamide

N-methylpyrrolidone  Dimethyl sulfoxide  Pyridine

Triethylamine  Diisopropylamine  1-Methyl-1H-tetrazole

1-Methylpyrazole  Pyrazine

Example 5 Method for Preparing Phosphoramidite Activator 5

Piperidine in an amount of 0.30 mL (3.04 mmol) was added to 29.70 mL of acetonitrile and dissolved to prepare a 1.0% by volume piperidine-added acetonitrile solution. Next, 1.73 g (9.00 mmol) of BTT was filled up to 30 mL with a 1.0% by volume piperidine-added acetonitrile solution to prepare a phosphoramidite activator 5 with 0.30 mol/L of BTT, containing 1.0% by volume of piperidine.

Examples 6 and 7 Method for Preparing Phosphoramidite Activators 6 and 7

Phosphoramidite activators 6 and 7 were prepared in the same manner as in Example 5, except that acetonitrile solutions to which 1.0% by volume of various additives described in Table 2 had been added were used instead of the 1.0% by volume piperidine-added acetonitrile solution.

Comparative Examples 13 to 15 Method for Preparing Phosphoramidite Activators 113 to 115

Phosphoramidite activators 113 to 115 were prepared in the same manner as in Example 5, except that acetonitrile solutions to which 1.0% by volume of various additives described in Table 2 had been added were used instead of the 1.0% by volume piperidine-added acetonitrile solution.

Experimental Example 2 Evaluation 2 of Storage Stability of Phosphoramidite Activator The presence or absence of precipitation (precipitation of BTT crystals) after leaving each of the phosphoramidite activators 5 to 7 obtained in Examples 5 to 7 and the phosphoramidite activators 113 to 115 obtained in Comparative Examples 13 to 15 to stand at 0° C. to 2° C. for one week and two weeks, respectively, was confirmed.

The evaluation results are shown in Table 2. In addition, a ratio of the molar concentration of the additive to the molar concentration of BTT is shown in Table 2 together with the evaluation results as "a ratio (%) to BTT".

TABLE 2

| | Molar concentration (mol/L) of BTT | Additive | | | | Presence or absence of precipitation | |
|---|---|---|---|---|---|---|---|
| | | Type | Addition amount | Molar concentratio n(mol/L) | Ratio (%) to BTT | After one week | After two weeks |
| Example 5: Phosphoramidite activator 5 | 0.30 | Piperidine | 1.0 | 0.101 | 33.7 | Absence | Absence |
| Example 6: Phosphoramidite activator 6 | 0.30 | N-methylpiperidine | 1.0 | 0.082 | 27.3 | Absence | Absence |
| Example 7: Phosphoramidite activator 7 | 0.30 | N-methylpyrrolidine | 1.0 | 0.096 | 32.0 | Absence | Absence |
| Comparative Example 13: Phosphoramidite activator 113 | 0.30 | N,N-dimethylformamide | 1.0 | 0.130 | 43.3 | Presence | Presence |
| Comparative Example 14: Phosphoramidite activator 114 | 0.30 | N-methylpyrrolidone | 1.0 | 0.104 | 34.7 | Presence | Presence |
| Comparative Example 15: Phosphoramidite activator 115 | 0.30 | Diisopropylamine | 1.0 | 0.071 | 23.7 | Presence | Presence |

From the results in Table 1, it was found that only piperidine, pyrrolidine, N-methylpiperidine, and N-methylpyrrolidine among the various additives can be stored for one week without causing precipitation. That is, it was proved that piperidine, pyrrolidine, N-methylpiperidine, and N-methylpyrrolidine are effective for improving the solubility of BTT in acetonitrile to store the phosphoramidite activator without precipitating BTT crystals.

Furthermore, from the results in Table 2, it was found that in a case where the amount of N-methylpiperidine and N-methylpyrrolidine to be added was increased from 0.5% by volume to 1.0% by volume, it was possible to store a product without causing precipitation even after 2 weeks. Therefore, the amount of N-methylpiperidine and N-methylpyrrolidine to be added was examined in detail.

Examples 8 to 13 Preparation of Phosphoramidite Activators 8 to 13

Phosphoramidite activators 8 to 13 were prepared in the same manner as in Example 3, except that the amounts of N-methylpiperidine to be added were 0.5%, 0.6%, 0.7%, 0.8%, 0.9%, and 1.0% by volume, respectively.

Examples 14 to 19 Method for Preparing Phosphoramidite Activators 14 to 19

Phosphoramidite activators 14 to 19 were prepared in the same manner as in Example 4, except that the amounts of N-methylpyrrolidine to be added were 0.5%, 0.6%, 0.7%, 0.8%, 0.9%, and 1.0% by volume, respectively.

Comparative Examples 16 to 18 Method for Preparing Phosphoramidite Activators 116 to 118

Phosphoramidite activators 116 to 118 were prepared in the same manner as in Example 1, except that N-methylimidazole was used as an additive instead of piperidine, and the addition amounts were 0.4%, 0.45%, and 0.5% by volume, respectively.

Experimental Example 3 Examination of Amount of Additive to be Added to Phosphoramidite Activator with 0.30 Mol/L of BTT The presence or absence of precipitation (precipitation of BTT crystals) after leaving each of the phosphoramidite activators 8 to 19 obtained in Examples 8 to 19 and the phosphoramidite activators 116 to 118 obtained in Comparative Examples 16 to 18 to stand at 0° C. to 2° C. for 2 weeks was confirmed.

The evaluation results are shown in Table 3. In addition, a ratio of the molar concentration of the additive to the molar concentration of BTT is shown in Table 3 together with the evaluation results as "a ratio (%) to BTT".

TABLE 3

| | Molar concentration (mol/L) of BTT | Additive | | | | absence of precipitation (after two weeks) |
| --- | --- | --- | --- | --- | --- | --- |
| | | Type | Addition amount | Molar concentration (mol/L) | Ratio (%) to BTT | |
| Example 8: Phosphoramidite activator 8 | 0.30 | N-methylpiperidine | 0.5 | 0.041 | 13.7 | Presence |
| Example 9: Phosphoramidite activator 9 | 0.30 | N-methylpiperidine | 0.6 | 0.049 | 16.3 | Presence |
| Example 10: Phosphoramidite activator 10 | 0.30 | N-methylpiperidine | 0.7 | 0.058 | 19.3 | Absence |
| Example 11: Phosphoramidite activator 11 | 0.30 | N-methylpiperidine | 0.8 | 0.066 | 22.0 | Absence |
| Example 12: Phosphoramidite activator 12 | 0.30 | N-methylpiperidine | 0.9 | 0.074 | 24.7 | Absence |
| Example 13: Phosphoramidite activator 13 | 0.30 | N-methylpiperidine | 1.0 | 0.082 | 27.3 | Absence |
| Example 14: Phosphoramidite activator 14 | 0.30 | N-methylpyrrolidine | 0.5 | 0.048 | 16.0 | Presence |
| Example 15: Phosphoramidite activator 15 | 0.30 | N-methylpyrrolidine | 0.6 | 0.058 | 19.3 | Absence |
| Example 16: Phosphoramidite activator 16 | 0.30 | N-methylpyrrolidine | 0.7 | 0.067 | 22.3 | Absence |
| Example 17: Phosphoramidite activator 17 | 0.30 | N-methylpyrrolidine | 0.8 | 0.077 | 25.7 | Absence |
| Example 18: Phosphoramidite activator 18 | 0.30 | N-methylpyrrolidine | 0.9 | 0.087 | 29.0 | Absence |
| Example 19: Phosphoramidite activator 19 | 0.30 | N-methylpyrrolidine | 1.0 | 0.096 | 32.0 | Absence |
| Comparative Example 16: Phosphoramidite activator 116 | 0.30 | N-methylimidazole | 0.4 | 0.051 | 17.0 | Presence |
| Comparative Example 17: Phosphoramidite activator 117 | 0.30 | N-methylimidazole | 0.45 | 0.058 | 19.3 | Absence |
| Comparative Example 18: Phosphoramidite activator 118 | 0.30 | N-methylimidazole | 0.5 | 0.063 | 21.0 | Absence |

Example 20 Method for Preparing Phosphoramidite Activator 20

BTT in an amount of 2.02 g (10.5 mmol) was filled up to 30 mL with a 0.5% by volume N-methylpiperidine-added acetonitrile solution to prepare a phosphoramidite activator 20 with 0.35 mol/L of BTT, containing 0.50% by volume of N-methylpiperidine.

Examples 21 to 25 Method for Preparing Phosphoramidite Activators 21 to 25

Phosphoramidite activators 21 to 25 were prepared in the same manner as in Example 20, except that the amounts of N-methylpiperidine to be added were 0.6%, 0.7%, 0.8%, 0.9%, and 1.0% by volume, respectively.

Examples 26 to 31 Method for Preparing Phosphoramidite Activators 26 to 31

Phosphoramidite activators 26 to 31 were prepared in the same manner as in Example 20, except that N-methylpyrrolidine was used as an additive instead of N-methylpiperidine, and the addition amounts were 0.5%, 0.6%, 0.7%, 0.8%, 0.9%, and 1.0% by volume, respectively.

Comparative Examples 19 to 24 Method for Preparing Phosphoramidite Activators 119 to 124

Phosphoramidite activators 119 to 124 in the same manner as in Example 20, except that N-methylimidazole was used as an additive instead of N-methylpiperidine, and the addition amounts were 0.5%, 0.6%, 0.7%, 0.8%, 0.9%, and 1.0% by volume, respectively.

Experimental Example 4 Examination of Amount of Additive to be Added to Phosphoramidite Activator with 0.35 Mol/L of BTT The presence or absence of precipitation (precipitation of BTT crystals) after leaving each of the phosphoramidite activators 20 to 31 obtained in Examples 20 to 31 and the phosphoramidite activators 119 to 124 obtained in Comparative Examples 19 to 24 to stand at 0° C. to 2° C. for 2 weeks was confirmed.

The evaluation results are shown in Table 4. In addition, a ratio of the molar concentration of the additive to the molar concentration of BTT is shown in Table 4 together with the evaluation results as "a ratio (%) to BTT".

TABLE 4

| | Molar concentration (mol/L) of BTT | Additive | | | | absence of precipitation (after two weeks) |
|---|---|---|---|---|---|---|
| | | Type | Addition amount | Molar concentration (mol/L) | Ratio (%) to BTT | |
| Example 20: Phosphoramidite activator 20 | 0.35 | N-methylpiperidine | 0.5 | 0.041 | 11.7 | Presence |
| Example 21: Phosphoramidite activator 21 | 0.35 | N-methylpiperidine | 0.6 | 0.049 | 14.0 | Presence |
| Example 22: Phosphoramidite activator 22 | 0.35 | N-methylpiperidine | 0.7 | 0.058 | 16.6 | Presence |
| Example 23: Phosphoramidite activator 23 | 0.35 | N-methylpiperidine | 0.8 | 0.066 | 18.9 | Presence |
| Example 24: Phosphoramidite activator 24 | 0.35 | N-methylpiperidine | 0.9 | 0.074 | 21.1 | Absence |
| Example 25: Phosphoramidite activator 25 | 0.35 | N-methylpiperidine | 1.0 | 0.082 | 23.4 | Absence |
| Example 26: Phosphoramidite activator 26 | 0.35 | N-methylpyrrolidine | 0.5 | 0.048 | 13.7 | Presence |
| Example 27: Phosphoramidite activator 27 | 0.35 | N-methylpyrrolidine | 0.6 | 0.058 | 16.6 | Presence |
| Example 28: Phosphoramidite activator 28 | 0.35 | N-methylpyrrolidine | 0.7 | 0.067 | 19.1 | Presence |
| Example 29: Phosphoramidite activator 29 | 0.35 | N-methylpyrrolidine | 0.8 | 0.077 | 22.0 | Absence |
| Example 30: Phosphoramidite activator 30 | 0.35 | N-methylpyrrolidine | 0.9 | 0.087 | 24.9 | Absence |
| Example 31: Phosphoramidite activator 31 | 0.35 | N-methylpyrrolidine | 1.0 | 0.096 | 27.4 | Absence |
| Comparative Example 19: Phosphoramidite activator 119 | 0.35 | N-methylimidazole | 0.5 | 0.063 | 18.0 | Presence |
| Comparative Example 20: Phosphoramidite activator 120 | 0.35 | N-methylimidazole | 0.6 | 0.076 | 21.7 | Presence |
| Comparative Example 21: Phosphoramidite activator 121 | 0.35 | N-methylimidazole | 0.7 | 0.088 | 25.1 | Absence |
| Comparative Example 22: Phosphoramidite activator 122 | 0.35 | N-methylimidazole | 0.8 | 0.101 | 28.9 | Absence |
| Comparative Example 23: Phosphoramidite activator 123 | 0.35 | N-methylimidazole | 0.9 | 0.114 | 32.6 | Absence |
| Comparative Example 24: Phosphoramidite activator 124 | 0.35 | N-methylimidazole | 1.0 | 0.126 | 36.0 | Absence |

From the results in Tables 3 and 4, it was proved that in a case of the phosphoramidite activator with 0.30 mol/L of BTT, the solubility of BTT was improved and BTT crystals did not precipitate by the addition of 0.7% by volume or more of N-methylpiperidine or 0.6% by volume or more of N-methylpyrrolidine to acetonitrile. In addition, it was proved that in a case of the phosphoramidite activator with 0.35 mol/L of BTT, the solubility of BTT was improved and BTT crystals did not precipitate by the addition of 0.9% by volume or more of N-methylpiperidine or 0.8% by volume or more of N-methylpyrrolidine to acetonitrile. Upon comparison of the presence or absence of precipitation by the ratio of the molar concentration of the additive to BTT, it was proved that in a case of the phosphoramidite activator with 0.30 mol/L of BTT, BTT crystals did not precipitate by the addition of N-methylpiperidine and N-methylpyrrolidine in the same amount (19.3%) as that of N-methylimidazole which is the additive disclosed in Japanese Literature 1 (JP2008-530092A). In addition, it was also proved that in a case of the phosphoramidite activator with 0.35 mol/L of BTT, BTT crystals did not precipitate even by the addition in a smaller amount than N-methylimidazole.

Next, in order to evaluate the performance of the phosphoramidite activator of the embodiment of the present invention in the liquid-phase synthesis, a nucleic acid dimer synthesis was performed in a liquid-phase system, using a phosphoramidite activator (phosphoramidite activator with 0.30 mol/L of BTT, containing 0.6% by volume of piperidine, 0.6% by volume of pyrrolidine, 0.8% by volume of N-methylpiperidine, or 0.7% by volume of N-methylpyrrolidine) which can be stored at a low temperature of 0° C. to 2° C. for 2 weeks. At the same time, the nucleic acid dimer synthesis was performed, using a phosphoramidite activator with 0.30 mol/L of BTT, containing 0.5% by volume of N-methylimidazole, and a phosphoramidite activator with 0.30 mol/L of BTT without additives, and the synthesis results were compared.

Synthesis Example 1 Method for Synthesizing 3',5'-O-Bis(tert-butyldimethylsilyl)thymidine Thymidine (manufactured by FUJIFILM Wako Pure Chemical Corporation) in an amount of 25.0 g (103 mmol) was dissolved in 75 mL of N,N-dimethylformamide (DMF) (manufactured by FUJIFILM Wako Pure Chemical Corporation) and 75 mL of tetrahydrofuran (THF) (manufactured by FUJIFILM Wako Pure Chemical Corporation) in a nitrogen atmosphere, and cooled to 5° C. Thereafter, 21.1 g (310 mmol) of imidazole (manufactured by FUJIFILM Wako Pure Chemical Corporation) and 68.2 g (258 mmol) of tert-butyldimethylsilyl trifluoromethanesulfonate (TBSOTf) (manufactured by FUJIFILM Wako Pure Chemical Corporation) were added to the obtained solution, and the mixture was stirred at room temperature for 3 hours. THF was removed under reduced pressure after the reaction, and then 100 mL of diisopropyl ether (manufactured by FUJIFILM Wako Pure Chemical Corporation), 50 mL of ethyl acetate (manufactured by FUJIFILM Wako Pure Chemical Corporation), 100 mL of ion exchange water, and 100 mL of saturated sodium chloride solution were added thereto to perform liquid separation, and the aqueous layer was extracted with a mixed solvent of 100 mL of diisopropyl ether and 50 mL of ethyl acetate. The organic layer was washed with 200 mL of saturated sodium chloride solution and then dried by the addition of sodium sulfate. After filtering sodium sulfate, the organic layer was removed under reduced pressure to quantitatively obtain 3',5'-O-bis(tert-butyldimethylsilyl)thymidine in the form of pale yellow crystals.

Synthesis Example 2 Method for Synthesizing 3'-O-(tert-Butyldimethylsilyl)thymidine The entire amount of 3',5'-O-bis(tert-butyldimethylsilyl)thymidine obtained in Synthesis Example 1 was dissolved in 194 mL of THF and 32 mL of ion exchange water, and cooled to 5° C. Thereafter, 32 mL of trifluoroacetic acid (TFA) (manufactured by FUJIFILM Wako Pure Chemical Corporation) was added dropwise to the obtained solution over 20 minutes, and the mixture was stirred at 3° C. to 5° C. for 4 hours. The pH was adjusted with 450 mL of a 1.0 mol/L aqueous sodium hydroxide solution, and the mixture was extracted twice with 300 mL of ethyl acetate. The organic layer was washed with 300 mL of saturated sodium chloride solution, sodium sulfate was then added thereto, and the mixture was dried. After filtering sodium sulfate, the organic layer was removed under reduced pressure. The obtained crude product was purified by silica gel column chromatography (dichloromethane:methanol=100:0 to 97:3), and the obtained crude product was recrystallized from 35 mL of ethyl acetate and 105 mL of hexane to obtain 13.0 g (yield 35%) of 3'-O-(tert-butyldimethylsilyl)thymidine in the form of white powder.

The reaction scheme of Synthesis Examples 1 and 2 is shown below.

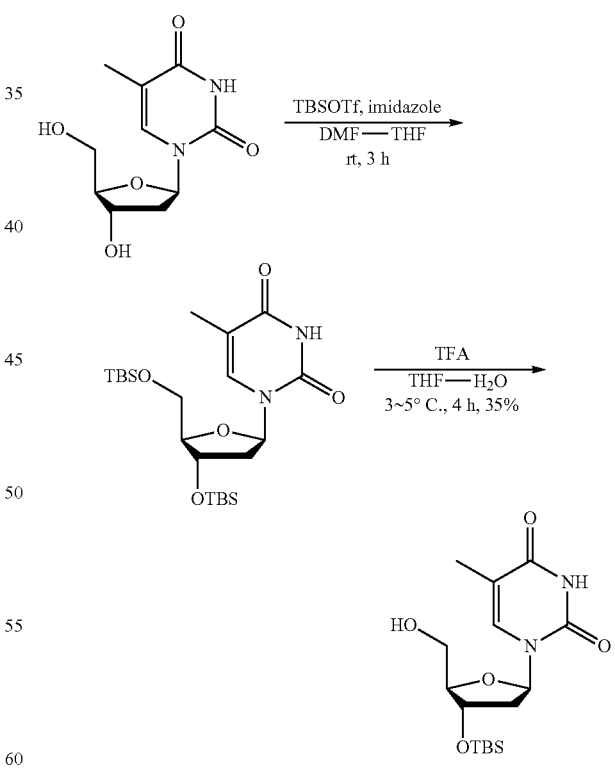

(In the reaction scheme, TBS represents a tert-butyldimethylsilyl group.)

Furthermore, it was confirmed that the physical property data of the obtained 3',5'-O-bis(tert-butyldimethylsilyl)thymidine are in agreement with the data described in J. Org. Chem. 2016, 81, 3848, and the physical property data of 3'-O-(tert-butyldimethylsilyl)thymidine are in agreement with the data described in Synlett 2018, 29, 2437.

Example 32 Synthesis of Nucleic Acid Dimer Using Phosphoramidite Activator 32

A phosphoramidite activator 32 with 0.30 mol/L of BTT, containing 0.6% by volume of piperidine, was prepared in the same manner as in Example 1, except that the amount of piperidine to be added was 0.6% by volume, instead of 0.5% by volume. Next, 752 mg (1.01 mmol) of 5'-O-(4,4'-dimethoxytrityl)thymidine-3'-[(2-cyanoethyl)-N,N-diisopropyl] phosphoramidite (manufactured by CARBOSYNTH Limited) and 300 mg (0.84 mmol) of 3'-O-(tert-butyldimethylsilyl)thymidine obtained in Synthesis Example 2 were charged in a nitrogen atmosphere, 6.73 mL of the phosphoramidite activator 32 was added thereto, and the mixture was stirred at room temperature for 15 minutes. Thereafter, 8.42 mL (8.42 mmol) of a 1.0 mol/L iodine solution (pyridine-water (9:1)) was added thereto, and the mixture was stirred at room temperature for 15 minutes. 84 mL of ethyl acetate and 84 mL of a 5% by mass aqueous sodium thiosulfate solution were added thereto to perform liquid separation, and the aqueous layer was extracted with 42 mL of ethyl acetate. The organic layer was washed with 84 mL of a 5% by mass aqueous sodium thiosulfate solution and dried by the addition of sodium sulfate. After filtering sodium sulfate, the organic layer was removed under reduced pressure. The obtained crude product was subjected to 1H NMR measurement and purified by silica gel column chromatography (hexane:ethyl acetate=4:6, ethyl acetate:methanol=98:2) to form 506 mg of a target pale yellow crystal-like nucleic acid dimer. The NMR and the isolation yields of the crude product were 64% and 59%, respectively. Furthermore, the NMR yield was calculated from an integrated value of 5.093 ppm of a target nucleic acid dimer, based on an integrated value of 3.322 ppm of a chemical shift, using dimethyl sulfone (manufactured by FUJIFILM Wako Pure Chemical Corporation) as an internal standard material.

The reaction scheme of Example 32 is shown below.

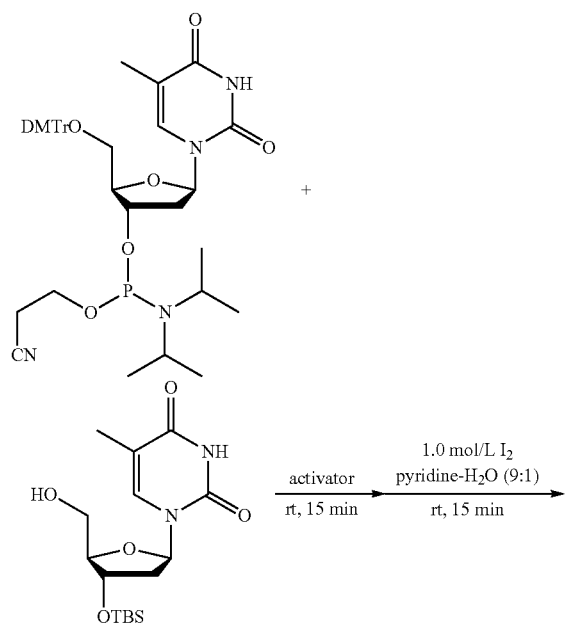

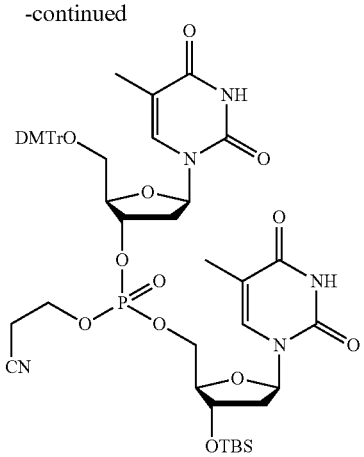

(In the reaction scheme, DMTr represents a 4,4'-dimethoxytrityl group and TBS represents a tert-butyldimethylsilyl group.)

Furthermore, it was confirmed that the physical property data of the obtained nucleic acid dimer were in agreement with the data described in J. Am. Chem. Soc. 2010, 132, 15930.

Example 33 Synthesis of Nucleic Acid Dimer Using Phosphoramidite Activator 33

A phosphoramidite activator 33 with 0.30 mol/L of BTT, containing 0.6% by volume of pyrrolidine, was prepared in the same manner as in Example 32, except that pyrrolidine was used instead of piperidine as an additive, and used to synthesize a nucleic acid dimer.

Example 34 Synthesis of Nucleic Acid Dimer Using Phosphoramidite Activator 11

A nucleic acid dimer was synthesized in the same manner as in Example 32, except that the phosphoramidite activator 11 obtained in Example 11 was used instead of the phosphoramidite activator 32.

Example 35 Synthesis of Nucleic Acid Dimer Using Phosphoramidite Activator 16

A nucleic acid dimer was synthesized in the same manner as in Example 32, except that the phosphoramidite activator 16 obtained in Example 16 was used instead of the phosphoramidite activator 32.

Comparative Example 24 Synthesis of Nucleic Acid Dimer Using Phosphoramidite Activator 101

A nucleic acid dimer was synthesized in the same manner as in Example 32, except that the phosphoramidite activator 101 obtained in Comparative Example 1 was used instead of the phosphoramidite activator 32.

Comparative Example 25 Synthesis of Nucleic Acid Dimer Using Phosphoramidite Activator 118

A nucleic acid dimer was synthesized in the same manner as in Example 32, except that the phosphoramidite activator 118 obtained in Comparative Example 18 was used instead of the phosphoramidite activator 32.

The yields calculated from NMR and the isolation yields after the purification by silica gel column chromatography in Examples 32 to 35 and Comparative Examples 24 and 25 are shown in Table 3. Furthermore, the physical property data of the products obtained in Examples 33 to 35 and Comparative Examples 24 and 25 were the same as those in Example 32.

TABLE 5

| | Molar concentration (mol/L) of BTT | Additive | | | Ratio (%) to BTT | NMR yield (%) | Isolation yield (%) |
|---|---|---|---|---|---|---|---|
| | | Type | Addition amount | Molar concentration (mol/L) | | | |
| Example 32: Phosphoramidite activator 32 | 0.30 | Piperidine | 0.6 | 0.061 | 20.3 | 61 | 57 |
| Example 33: Phosphoramidite activator 33 | 0.30 | Pyrrolidine | 0.6 | 0.072 | 24.0 | 59 | 55 |
| Example 34: Phosphoramidite activator 11 | 0.30 | N-methylpiperidine | 0.8 | 0.066 | 22.0 | 64 | 59 |
| Example 35: Phosphoramidite activator 16 | 0.30 | N-methylpyrrolidine | 0.7 | 0.067 | 22.3 | 65 | 59 |
| Comparative Example 24: Phosphoramidite activator 101 | 0.30 | (None) | — | — | — | 59 | 54 |
| Comparative Example 25: Phosphoramidite activator 118 | 0.30 | N-methylimidazole | 0.5 | 0.063 | 21.0 | 46 | 45 |

As seen from the results in Table 5, in a case where the N-methylimidazole-containing phosphoramidite activator disclosed in Patent Literature 1 was used, the yield of the obtained nucleic acid dimer was low upon comparison with a case where the phosphoramidite activator containing no additive was used. On the other hand, it was proved that in a case where the phosphoramidite activator of the embodiment of the present invention, containing piperidine, pyrrolidine, N-methylpiperidine, or N-methylpyrrolidine, is used, the reaction proceeds in a yield equal to or higher than that in a case where the phosphoramidite activator containing no additive is used, and the yield is thus not reduced. It was proved that particularly in a case where the phosphoramidite activator of the embodiment of the present invention, containing N-methylpiperidine or N-methylpyrrolidine among those, is used, the reaction proceeds in a yield higher than that in a case where the phosphoramidite activator containing no additive is used.

Therefore, it was found that the phosphoramidite activator of the embodiment of the present invention has excellent effects that it has higher storage stability than that of the additive (N-methylimidazole)-containing phosphoramidite activator disclosed in Patent Literature 1 in the liquid-phase synthesis, and has a reaction yield equal to or higher than that of the phosphoramidite activator containing no additive.

Next, in order to evaluate the performance of the phosphoramidite activator of the embodiment of the present invention in solid-phase synthesis, DNA oligomer synthesis was carried out in a solid-phase system, using a phosphoramidite activator with 0.30 mol/L of BTT (a phosphoramidite activator containing 0.7% by volume of N-methylpyrrolidine or 0.8% by volume of N-methylpiperidine) having good performance in the liquid-phase synthesis. At the same time, DNA oligomer synthesis using a phosphoramidite activator with 0.30 mol/L of BTT, containing 0.5% by volume of N-methylimidazole, was also performed, and the synthesis results were compared.

Example 36 Synthesis of DNA Oligomer Using Phosphoramidite Activator 11

A reaction column was filled with a universal support (carrier for solid-phase synthesis, trade name: Glen Unysupport CPG 1000, manufactured by Glen Research) in an amount equivalent to 1.0 µmol to prepare a 0.07 M acetonitrile solution of 5'-O-(4,4'-dimethoxytrityl)thymidine-3'-[(2-cyanoethyl)-N,N-diisopropyl]phosphoramidite (manufactured by CARBOSYNTH Limited) and the phosphoramidite activator 11 obtained in Example 11, and a dT 20mer (5'-TTTTTTTTTTTTTTTTTTTT-3') was synthesized using an NTS M-2-MX DNA/RNA synthesizer (manufactured by Nihon Techno Service Co., Ltd.). Furthermore, for the reactants, a 3% by mass dichloroacetic acid-toluene solution (manufactured by Sigma-Aldrich) was used as a deblocking reagent, a Cap A reagent (N-methylimidazole-acetonitrile solution (2:8)) (manufactured by FUJIFILM Wako Pure Chemical Corporation) and a Cap B reagent (acetic anhydride-2,6-lutidine-acetonitrile solution (2:3:5)) (manufactured by FUJIFILM Wako Pure Chemical Corporation) were used as a capping reagent, and a 0.05 M iodine solution (pyridine-water (9:1)) (manufactured by FUJIFILM Wako Pure Chemical Corporation) was used as an oxidizing reagent. After the synthesis, the obtained DNA oligonucleotide was immersed in a 28% by mass aqueous ammonia at 55° C. for 15 hours, and a dT 20mer was cleaved from the solid support and deprotected. The purity of a sample solution of the obtained dT 20mer was measured by high performance liquid chromatography (HPLC) (measurement conditions: column; Wakopak (registered trademark) Ultra C18-5 4.6 mm×150 mm, flow rate; 1.0 mL/min, column temperature; 40° C., UV detection wavelength: 260 nm, eluent A; 0.1 M aqueous triethylammonium acetate (TEAA) solution (pH 7.0), eluent B; 50% acetonitrile in 0.1 M aqueous TEAA solution (pH 7.0)).

Example 37 Synthesis of DNA Oligomer Using Phosphoramidite Activator 16

A dT 20mer was synthesized in the same manner as in Example 36, except that the phosphoramidite activator 16 obtained in Example 16 was used instead of the phosphoramidite activator 11, and a purity of the dT 20mer was measured by HPLC.

Comparative Example 26 Synthesis of DNA Oligomer Using Phosphoramidite Activator 118

A dT 20mer was synthesized in the same manner as in Example 36, except that the phosphoramidite activator 118 obtained in Comparative Example 18 was used instead of the phosphoramidite activator 11, and a purity of the dT 20mer was measured by HPLC.

The purity of the dT 20mers measured by HPLC in Examples 36 and 37 and Comparative Example 26 is shown in Table 6.

fluoride (TREAT-3HF) were added thereto, and deprotection of the tert-butyldimethylsilyl group was carried out by being immersed at 60° C. for 3 hours. The purity of the obtained rU 20mer was measured by HPLC under the same measurement conditions as in Example 36.

TABLE 6

| | Molar concentration (mol/L) of | Additive | | | Ratio (%) to BTT | HPLC purity (% by area) |
|---|---|---|---|---|---|---|
| | | Type | Addition amount | Molar concentration (mol/L) | | |
| Example 36: Phosphoramidite activator 11 | 0.30 | N-methylpiperidine | 0.8 | 0.066 | 22.0 | 72.3 |
| Example 7: Phosphoramidite activator 16 | 0.30 | N-methylpyrrolidine | 0.7 | 0.067 | 22.3 | 72.9 |
| Comparative Example 26: Phosphoramidite activator 118 | 0.30 | N-methylimidazole | 0.5 | 0.063 | 21.0 | 72.2 |

Next, RNA oligomer synthesis was carried out in a solid-phase system, using a phosphoramidite activator (a phosphoramidite activator with 0.30 mol/L of BTT, containing 0.8% by volume of N-methylpiperidine or 0.7% by volume of N-methylpyrrolidine). At the same time, the RNA oligomer synthesis was performed, using a phosphoramidite activator with 0.30 mol/L of BTT, containing 0.5% by volume of N-methylimidazole, and the synthesis results thereof were compared.

Example 38 Synthesis of RNA Oligomer Using Phosphoramidite Activator 11

A reaction column was filled with a universal support (a carrier for solid-phase synthesis, trade name: Glen Unysupport CPG 1000, manufactured by Glen Research) in an amount equivalent to 0.2 μmol to prepare a 0.07 M acetonitrile solution of 5'-O-(4,4'-dimethoxytrityl)-2'-O-(tert-butyldimethylsilyl)uridine-3'-[(2-cyanoethyl)-N,N-diisopropyl]phosphoramidite (manufactured by Sigma-Aldrich) and the phosphoramidite activator 11 obtained in Example 11, and a rU 20mer (5'-UUUUUUUUUUUUUUUUUUUU-3') was synthesized using an NTS M-2-MX DNA/RNA synthesizer (manufactured by Nihon Techno Service Co., Ltd.). It should be noted that the same reactant as described in Example 36 was used as the reactant. After the synthesis, the obtained DNA oligonucleotide was immersed in a mixed solvent of 28% by mass aqueous ammonia-40% by mass aqueous methylamine solution-70% by mass aqueous ethanol solution (1:1:1) at 60° C. for 3 hours, and the rU 20mer was cleaved from the solid support and deprotected. Furthermore, the obtained solution was concentrated, 50 μL of dimethyl sulfoxide and 200 μL of triethylamine trihydro- Example 39 Synthesis of RNA Oligomer Using Phosphoramidite Activator 16

A rU 20mer was synthesized in the same manner as in Example 38, except that the phosphoramidite activator 16 obtained in Example 16 was used instead of the phosphoramidite activator 11, and a purity of the rU 20mer was measured by HPLC.

Comparative Example 27 Synthesis of RNA Oligomer Using Phosphoramidite Activator 118

A rU 20mer was synthesized in the same manner as in Example 38, except that the phosphoramidite activator 118 obtained in Comparative Example 18 was used instead of the phosphoramidite activator 11, and a purity of the rU 20mer was measured by HPLC.

The purity of rU 20mer measured by HPLC in Examples 38 and 39 and Comparative Example 27 is shown in Table 7.

TABLE 7

| | Molar concentration (mol/L) of | Additive | | | Ratio (%) to BTT | HPLC purity (% by area) |
|---|---|---|---|---|---|---|
| | | Type | Addition amount | Molar concentration (mol/L) | | |
| Example 38: Phosphoramidite activator 11 | 0.30 | N-methylpiperidine | 0.8 | 0.066 | 22.0 | 27.7 |
| Example 39: Phosphoramidite activator 16 | 0.30 | N-methylpyrrolidine | 0.7 | 0.067 | 22.3 | 28.1 |
| Comparative Example 27: Phosphoramidite activator 118 | 0.30 | N-methylimidazole | 0.5 | 0.063 | 21.0 | 24.8 |

From the results in Tables 6 and 7, it was proved that even in a case where the phosphoramidite activator of the embodiment of the present invention, containing N-methylpiperidine or N-methylpyrrolidine, is used for solid-phase synthesis, DNA/RNA oligomers can be obtained in a purity equal to or higher than that in a case where the N-methylimidazole-containing phosphoramidite activator disclosed in Patent Literature 1 is used.

Therefore, it was found that the phosphoramidite activator of the embodiment of the present invention has excellent effects that it has high storage stability equal to or higher than that of the additive (N-methylimidazole)-containing phosphoramidite activator disclosed in Patent Literature 1 in solid-phase synthesis, and a target product can be obtained in a high purity equal to or higher than that of the phosphoramidite activator disclosed in the literature.

The invention claimed is:

1. A phosphoramidite activator comprising:
   (i) at least one compound selected from the group consisting of piperidine, pyrrolidine, N-alkylpiperidine, and N-alkylpyrrolidine;
   (ii) 5-benzylthio-1H-tetrazole; and
   (iii) acetonitrile.

2. The phosphoramidite activator according to claim 1, wherein (i) is N-alkylpiperidine or N-alkylpyrrolidine.

3. The phosphoramidite activator according to claim 1, wherein (i) is N-methylpiperidine or N-methylpyrrolidine.

4. The phosphoramidite activator according to claim 1, wherein a molar concentration of (ii) is 0.25 mol/L or more.

5. The phosphoramidite activator according to claim 1, wherein a molar concentration of piperidine of (i) is 17.0% or more with respect to a molar concentration of (ii), a molar concentration of pyrrolidine of (i) is 20.0% or more with respect to the molar concentration of (ii), a molar concentration of N-alkylpiperidine of (i) is 13.7% or more with respect to the molar concentration of (ii), and a molar concentration of N-alkylpyrrolidine of (i) is 16.0% or more with respect to the molar concentration of (ii).

6. The phosphoramidite activator according to claim 1, wherein a molar concentration of piperidine of (i) is 17.0% or more with respect to a molar concentration of (ii), a molar concentration of pyrrolidine of (i) is 24.0% or more with respect to the molar concentration of (ii), and a molar concentration of N-alkylpiperidine or N-alkylpyrrolidine of (i) is 19.3% or more with respect to the molar concentration of (ii).

7. A method for activating a phosphoramidite, comprising:
   reacting a phosphoramidite with the phosphoramidite activator according to claim 1.

8. The method for activating a phosphoramidite according to claim 7, wherein the phosphoramidite is a compound represented by the following general formula (I):

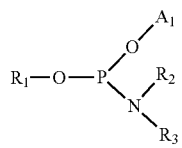

(I)

in the general formula (I), $R_1$ represents a group selected from the following group (I-1) of functional groups:

Group (I-1) of functional groups

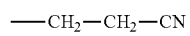

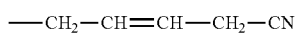

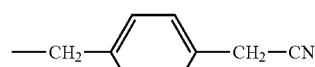

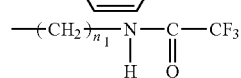

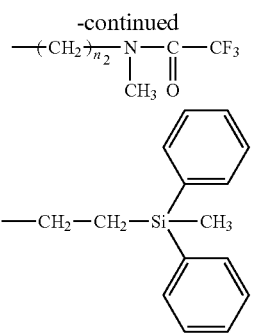

in the group (I-1) of functional groups, $n_1$ and $n_2$ each independently represent an integer of 1 to 6, and $R_2$ and $R_3$ each independently represent an alkyl group having 1 to 6 carbon atoms, $R_2$ and $R_3$ may be bonded to form a 5- to 7-membered heterocyclic structure, and $A_1$ represents a nucleoside.

9. A method for synthesizing a phosphate ester or a thiophosphate ester, comprising:
   (1) reacting a phosphoramidite with a nucleoside or an oligonucleotide in the presence of the phosphoramidite activator according to claim 1 to produce a phosphite ester; and
   (2) oxidizing or sulfurizing the phosphite ester to produce a phosphate ester or a thiophosphate ester.

10. The method for synthesizing a phosphate ester or a thiophosphate ester according to claim 9, wherein the phosphoramidite is a compound represented by the following general formula (I), the phosphate ester is a compound represented by the following general formula (II-1), and the thiophosphate ester is a compound represented by the following general formula (II-2):

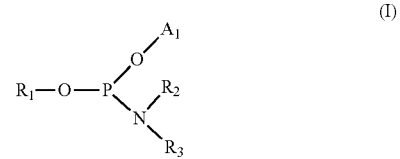

(I)

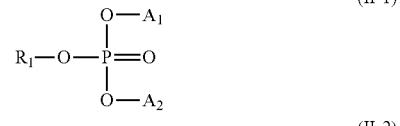

(II-1)

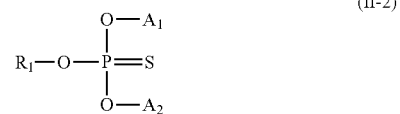

(II-2)

in the general formulae (I), (II-1), and (II-2), $R_1$ represents a group selected from the following group (I-1) of functional groups:

Group (I-1) of functional groups

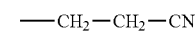

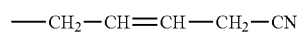

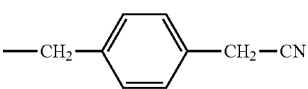

-continued
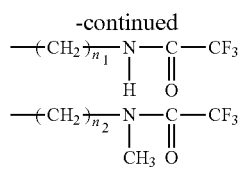
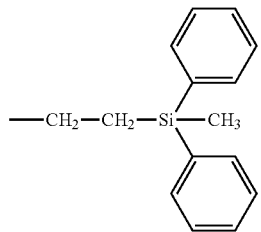
in the group (I-1) of functional groups, $n_1$ and $n_2$ each independently represent an integer of 1 to 6, and
$R_2$ and $R_3$ each independently represent an alkyl group having 1 to 6 carbon atoms, $R_2$ and $R_3$ may be bonded to form a 5- to 7-membered heterocyclic structure, $A_1$ represents a nucleoside, and $A_2$ represents a nucleoside or an oligonucleotide.
\* \* \* \* \*